United States Patent

Brokowski et al.

[11] Patent Number: 5,549,001
[45] Date of Patent: Aug. 27, 1996

[54] SET OF ULTRASONIC PROBEHEADS FOR MEASUREMENTS OF TIMES OF FLIGHT OF ULTRASONIC PULSES

[75] Inventors: Andrzej Brokowski; Jacek Szelążek, both of Warsaw, Poland

[73] Assignee: Instytut Podstawowych Problemów Techniki, Warsaw, Poland

[21] Appl. No.: 185,887

[22] PCT Filed: Jul. 22, 1992

[86] PCT No.: PCT/PL92/00009

§ 371 Date: Mar. 28, 1994

§ 102(e) Date: Mar. 28, 1994

[87] PCT Pub. No.: WO93/03361

PCT Pub. Date: Feb. 18, 1993

[30] Foreign Application Priority Data

Jul. 27, 1991 [PL] Poland .................. 290830

[51] Int. Cl.[6] .................. G01H 5/00
[52] U.S. Cl. .................. 73/597; 73/644
[58] Field of Search .................. 73/597, 598, 628, 73/632, 642, 644

[56] References Cited

U.S. PATENT DOCUMENTS

| | | | |
|---|---|---|---|
| 4,313,070 | 1/1982 | Fisher | 73/644 |
| 4,372,163 | 2/1983 | Tittmann | 73/597 |
| 4,398,421 | 8/1983 | White | 73/644 |
| 4,712,428 | 12/1987 | Ishii | 73/644 |

*Primary Examiner*—Hezron E. Williams
*Assistant Examiner*—Christine K. Oda
*Attorney, Agent, or Firm*—Horst M. Kasper

[57] ABSTRACT

A set of ultrasonic probes for measurement of time of flight of ultrasonic pulses includes a housing (20), two transmitting ultrasonic probes (1, 2) and two identical receiving ultrasonic probes (9, 10) attached to the housing (20). The receiving ultrasonic probes (9, 10) are disposed between the transmitting ultrasonic probes (1, 2) and are disposed along one line with the transmitting ultrasonic probes (1, 2). Time $t_L$ of flight of wave pulse in the workpiece along the distance L between the receiving ultrasonic probes (9, 10) is calculated based on propagation time of a ultrasonic wave (7) transmitted by the transmitting ultrasonic probe (1) and received by the receiving ultrasonic probeheads (9, 10) and on propagation time of a ultrasonic wave (8) transmitted by the transmitting ultrasonic probehead (2) and received by the receiving ultrasonic probeheads (9, 10).

3 Claims, 2 Drawing Sheets

SET OF ULTRASONIC PROBEHEADS FOR MEASUREMENTS OF TIMES OF FLIGHT OF ULTRASONIC PULSES

CROSS-REFERENCE TO RELATED APPLICATIONS

This application is a continuation-in-part application of another international application filed Jul. 22, 1992 under the Patent Cooperation Treaty and bearing this application No. PCT/PL92/00009. The entire disclosure this application, including the drawings thereof, is hereby incorporated in this application as if fully set forth herein.

U.S. Pat. Nos.
  4,398,421 8/1983 White
  4,372,163 2/1983 Tittmann
FOREIGN PATENT DOCUMENTS
  13 8042 4/1987 Poland
OTHER PUBLICATIONS
  E. Schneider et al., Automatisierte Bestimmungoberflaschennaher Spannungszustande in Waltzen mittels Ultraschallverfahren, Mat. Konf. DGZfP, September 1989, Kiel, pp. 419–425.

BACKGROUND OF THE INVENTION

This invention relates to the measurement of ultrasonic subsurface waves velocities. Times of flight or velocities of such waves are used to evaluate elastic properties, texture or stresses in materials under test. Subsurface waves are desirable when the access is limited to only one surface of the workpiece or only surface layer of the workpiece material is to be evaluated.

For these measurements various sets of ultrasonic probes are used. The basic set consisting of one transmitting and one receiving probeheads is described in U.S. Pat. No. 4,398,421 to White. Both probes are equipped with piezoelectric crystals and plastic wedges and are acoustically coupled to the workpiece surface by means of a coupling medium. The velocity of subsurface wave is determined by measuring the time between the transmission by the first crystal and reception by the second crystal and factoring the measured time into the predetermined distance.

Another method to determine the velocity of surface wave is described in U.S. Pat. No. 4,372,163 to Tittmann. A pair of probes, one transmitting and one receiving surface wave, is used. Two times between the transmitting and receiving crystals are measured for two various distances between probes. The velocity of waves is determined by factoring the difference in measured times into the difference in distances between probes.

The so-called "differential set of probes", consisting of one transmitting probe and two receiving probes, arranged along one line, is described in Polish Patent 13 8042 to Borkowski et al. and by E. Schneider et al., Automatisierte Bestimmungoberflaschennaher Spannungszustande in Walzen mittels Ultraschallverfahren, Mat. Konf. DGZfP, pp. 419–425 (Kiel 1989). Two times of subsurface wave are measured: the first one between transmission by the transmitting crystal and reception by the first receiving crystal, and the second one between the transmitting crystal and the reception by the second receiving crystal. The velocity of wave is determined by factoring the difference of measured times into the distance between receiving probes.

The weakness of the known sets of ultrasonic probes is that their performances can be easily adversely affected by the temperature or the roughness of surface of the workpiece under test. Ultrasonic subsurface or surface wave transmitted by the crystal of the first probes in order to be detected by the crystal of the second probe, has to travel all the way long through the wedge, coupling medium layer and workpiece surface layer and also through the second layer of coupling medium and the second wedge. The time of flight of ultrasonic wave in the plastic wedge is strongly dependent on the wedge temperature.

Time of propagation of such waves between crystals is also dependent on the thicknesses of the layers of the coupling medium. These thicknesses are functions of the workpiece roughness which can vary over the workpiece surface.

Assuming the temperature of the wedges in both receiving probes of "differential set" are the same, due to the fact that the set consists of one transmitting and two receiving probes, the influence of temperature on measured time is eliminated. Also in the method described in U.S. Pat. No. 4,372,163 the influence of temperature is eliminated. However, for all known sets of probes, the determined velocity of subsurface or surface waves still depends on irregularities of the workpiece surface roughness. Due to these irregularities the thickness of the layer of the coupling medium between the wedge of each probe and the workpiece surface can be different. To eliminate the influence of surface roughness on results obtained with known sets of probes it is necessary to prepare the workpiece surface.

It is an object of this invention to provide a novel and improved method for measuring the velocity of ultrasonic subsurface waves in a workpiece with rough surfaces, without time-consuming surface preparation. Railroad rails and other rolled products provide a good example of workpieces with rough surfaces, in which velocities of subsurface waves are to be measured in order to determine residual stresses or texture. The features of our invention will be understood from the study of the following description and drawings showing preferred embodiment of the invention.

SUMMARY OF THE INVENTION

A set of ultrasonic probes has been developed to measure the velocity of ultrasonic subsurface waves in workpieces with rough surfaces. As opposed to known devices, our set consists of several probes arranged along one line. Two probes are used to generate subsurface waves in the workpiece. These waves are propagated along one line but in opposite directions. Two identical receiving probes are positioned between transmitting probes. Each of the receiving probes is equipped with one plastic wedge and two piezoelectric crystals and can receive subsurface waves propagated in opposite directions.

Probes are acoustically coupled with the workpiece surface by means of a coupling medium. The thicknesses of medium layers between probes and workpiece depend on the roughness of the workpiece surface. To eliminate the influence of the workpiece surface roughness on velocity to be determined, times of flight of waves propagated in opposite directions are measured. Mean values of these times are not influenced by variations in the thickness of layers of the coupling medium. Velocity of the subsurface wave can be determined by factoring mean value of time into a distance between the receiving probes.

DESCRIPTION OF THE PREFERRED EMBODIMENT

Figure 1:
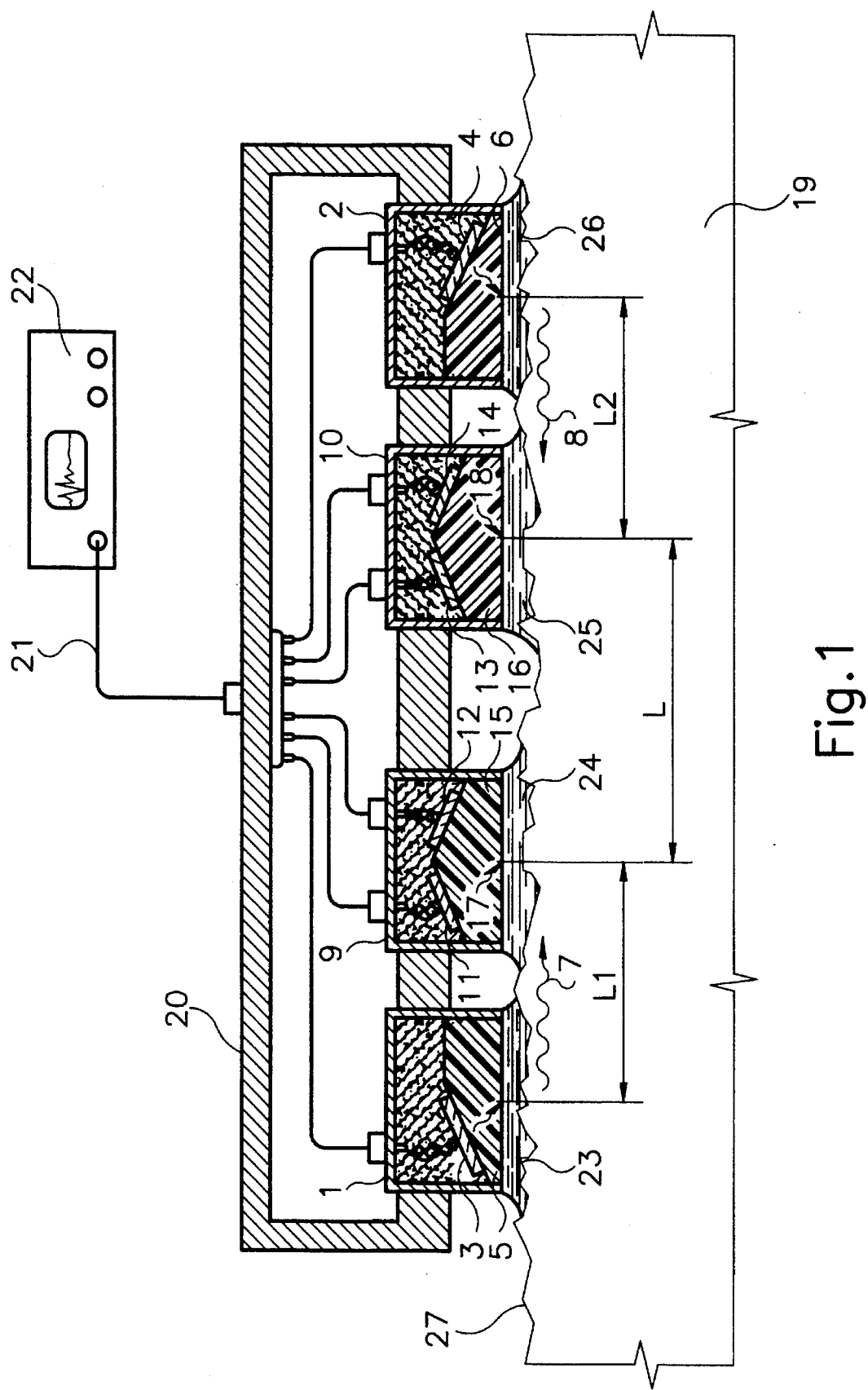
FIG. 1 is a schematic diagram of a set of ultrasonic probes which may be used to practice the method of the invention.

The preferred embodiment is shown in FIG. 1. The device is a set of four ultrasonic probes embedded in a housing and directed to generate and receive ultrasonic subsurface waves propagated along the surface of a tested workpiece. The set of probes is connected by means of a cable 21 to an electronic circuit assembly 22. The assembly 22 measures times of flight of ultrasonic waves.

As shown in FIG. 1, four ultrasonic probes generally designated by numerals 1,2,9,10 are embedded in a housing block 20. The distances between probes 1,2,9,10 are fixed. The distance between the receiving probes 9,10 is denoted as L, the distance between the transmitting probe 1 and the receiving probe 9 is denoted as L1 and the distance between the transmitting probe 2 and the receiving probe 10 is denoted as L2. The set of probes is positioned on a rough surface 27 of the workpiece 19 and is acoustically coupled with it by means of a coupling medium. The thicknesses of the coupling medium layers 23,24,25,26 between probes 1,9,10,2, respectively and workpiece surface 27 depend on a local roughness of the workpiece surface 27.

Each of the transmitting probes 1,2 consists of wedges 5,6 and piezoelectric crystals 3,4, respectively. Longitudinal waves transmitted from crystals 3,4 are propagated through wedges 5,6 and layers 23, 26 of the coupling medium, respectively. Upon contact with the surface 27 of the workpiece 19, according to Snell's law, these waves are converted to subsurface waves 7,8. Waves 7,8 are propagated along one line parallel to the surface 27 but in opposite directions.

Each of the receiving probes 9,10 is composed of a wedge 15,16 and two piezoelectric crystals 11,12 and 13,14, respectively. Below the wedge 15 of the receiving probe 9, according to Snell's law, the subsurface wave 7 is partly converted to a longitudinal wave and passes upwardly through the layer of the coupling medium 24, wedge 15 and finally is converted to an electric pulse by the crystal 12. Below the wedge 16 of the receiving probe 10, the subsurface wave 7 is again partly converted to the longitudinal one and passes upwardly through the layer 25 of the coupling medium, wedge 16 and is converted to an electrical pulse by the crystal 14. Subsurface wave 8, propagated in opposite direction to the wave 7, below wedges 15,16 is partly converted to longitudinal waves which pass upwardly through the layers 24,25 of the coupling medium, wedges 15,16 and are converted to electrical pulses by crystals 11,13.

Figure 2:
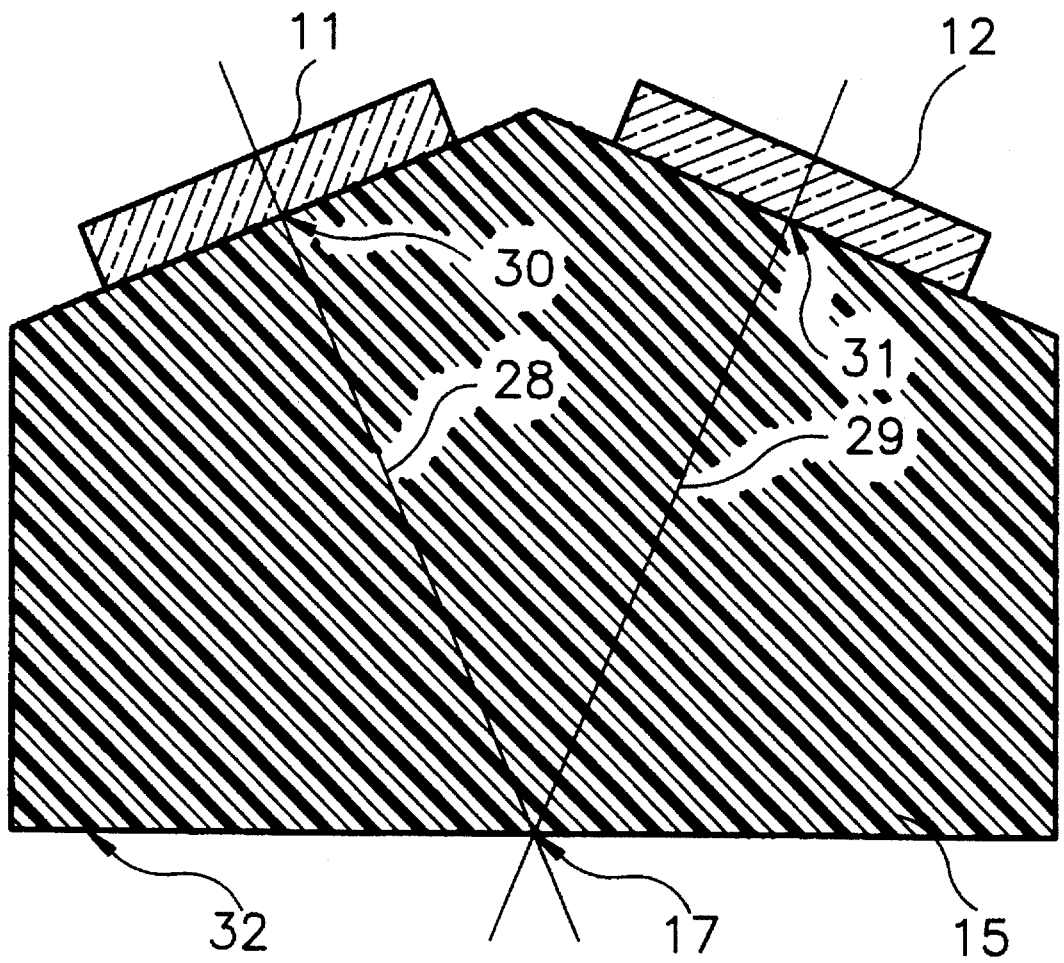
FIG. 2 shows in details the geometry of the wedge of a receiving probe.

Wedges 15,16 of receiving probes 9,10 are made of the same material and their shapes and dimensions are identical. Also the shapes and dimensions of four crystals 11,12,13,14 mounted on wedges 15,16 are identical. FIG. 2 shows details of the geometry of the wedge and positions of crystals on the wedge of the receiving probe 9. The wedge 15 and crystals 11,12 are designed in such a manner that the point of intersection 17 of two lines 28,29, perpendicular to the surfaces of crystals 11,12 and guided from the crystals centers 30,31, is situated on the bottom surface 32 of the wedge 15. The distances between the point 17 and crystals centers 30,31 are the same. In the wedge 16, the point of intersection of two lines perpendicular to the surfaces of crystals 13,14 and guided from their centers, is situated on the bottom surface of the wedge 16 and is designated by the numeral 18. The distances between the point 18 and centers of crystals 13,14 are the same and equal to the distances between the point 17 and centers of crystals 11,12.

In order to eliminate the influence of the workpiece surface 27 roughness on the determined velocity of the subsurface wave, there are measured times of flight of waves 7 and 8 propagated in opposite directions. In the first step crystal 3 is driven to transmit wave the 7 and times of flight of wave 7 $t_{3-12}$ and $t_{3-14}$ are measured. Time $t_{3-12}$ is the time of propagation of wave 7 between crystal 3 and crystal 12, time $t_{3-14}$ is the time of propagation of wave 7 between crystal 3 and 14. These times are described as $$t_{3-12}=t_5+t_{23}+t_{L1}+t_{24}+t_{15}$$

$$t_{3-14}=t_5+t_{23}+t_{L1}+t_L+t_{25}+t_{16}$$

where $t_5$ is time of flight of wave 7 in the wedge 5, $t_{23}$ is time of flight of wave 7 through the layer 23 of the coupling medium, $t_{L1}$ is time of flight of wave 7 in the workpiece from the transmitting probe 1 to the receiving probe 9, $t_{24}$ is time of flight of wave 7 through the layer 24 of the coupling medium, $t_{15}$ is time of flight of wave 7 in the wedge 15, $t_L$ is time of flight of wave 7 in the workpiece on distance L between receiving probes 9,10, and determined by points 17,18, $t_{25}$ is time of flight of wave 7 through the layer 25 of the coupling medium, $t_{16}$ is time of flight of wave 7 in the wedge 16.

In the second step the crystal 4 is driven to transmit the wave 8 and there are measured times $t_{4-13}$ and $t_{4-11}$. Time $t_{4-13}$ is the time of propagation of wave 8 between crystal 4 and crystal 13. Time $t_{4-11}$ is the time of propagation of wave 8 between crystal 4 and crystal 11. These two times are described as $$t_{4-13}=t_6+t_{26}+t_{L2}+t_{25}+t_{16}$$

$$t_{4-11}=t_6+t_{26}+t_{L2}+t_L+t_{24}+t_{15}$$

where $t_6$ is time of flight of wave 8 in the wedge 6, $t_{26}$ is time of flight through the layer 26 of the coupling medium, $t_{L2}$ is time of flight in the workpiece from the transmitting probe 2 to the receiving probe 10, $t_{25}$ is time of flight of wave 8 through the layer 25 of the coupling medium, $t_{16}$ is time of flight of wave 8 in the wedge 16.

$t_{24}$ is time of flight of wave 8 through the layer 24 of the coupling medium, $t_{15}$ is time of flight of wave 8 in the wedge 15, $t_L$ is time of flight of wave 8 in the workpiece on distance L between receiving probes 9,10, and determined by points 17,18.

In the third step the mean value $t_L$ of times of flight of waves 7 and 8 in the workpiece, along the distance L between receiving probes 9,10, is calculated as $$t_L=(t_{3-14}+t_{4-11}-t_{3-12}-t_{4-13})/2$$

and is not dependent on the thickness of the coupling medium layers 23,24,25,26. Velocity of subsurface wave can be determined by factoring time $t_L$ into the distance L.

Thus it can be seen that the present invention provides an improved set of probes for measuring the velocity of ultrasonic subsurface waves in a workpiece with a rough surface. Depending on the angle of wedges 5,6,15,16, the set of probes can be used for measuring velocities of the subsurface longitudinal wave or subsurface shear waves polarized in vertical (the so-called SV wave) or horizontal (the so-called SH wave) directions.

What is claimed is:

1. A set of ultrasonic probeheads for measurements of times of flight of surface skimming wave pulses comprising:

two transmitting ultrasonic probeheads generating ultrasonic waves where the ultrasonic waves propagate in the material being tested along one line but in opposite directions and two identical receiving ultrasonic probeheads arranged in one line with said transmitting ultrasonic probeheads and disposed between said two transmitting ultrasonic probeheads, wherein each one of said receiving ultrasonic probeheads includes two receiving transducers and wherein each one of said receiving transducers receives ultrasonic waves from opposite directions, and wedges of the receiving ultrasonic probeheads, where distances determined by centers of said receiving transducers and point of intersection of lines normal to transducers going from said centers are equal and said points of intersection lie on bottom surfaces of the wedges, wherein said receiving transducers in each one of said receiving ultrasonic probeheads are mounted on a common wedge of said wedges.

2. A set of ultrasonic probes for determining time of flight of subsurface waves comprising:

two transmitting probes generating subsurface waves in a workpiece propagated along one line but in opposite directions, and two identical receiving probes arranged in one line with said transmitting probes wherein the two identical receiving probes are disposed between the two transmitting probes, and wherein each of said two identical receiving probes is equipped with one wedge and two piezoelectric crystals and wherein each of said two identical receiving probes is detecting waves generated by said two transmitting probes and propagated in opposite directions, and wherein wedges of said two identical receiving probes are shaped so that lines perpendicular to two said piezoelectric crystals mounted on said wedges and perpendicular to said crystals surfaces, intersect on bottom surfaces of said wedges and the distance between piezoelectric crystals centers and point of lines intersections are the same.

3. A set of ultrasonic probes for determining time of flight of subsurface waves comprising:

two transmitting probes generating subsurface waves in the workpiece propagated along one line but in opposite directions, and two identical receiving probes arranged in one line with said transmitting probes, wherein the two identical receiving probes are disposed between the two transmitting probes, and wherein each of said receiving probes is equipped with one wedge and two piezoelectric crystals and wherein each of said receiving probes is detecting waves generated by said transmitting probes and propagated in opposite directions, and wherein each said wedge of said receiving probes shaped so that lines perpendicular to two said piezoelectric crystals mounted on said wedges and perpendicular to said crystals surfaces intersect on the bottom surfaces of said wedges and the distance between piezoelectric crystals centers and point of lines intersections are the same.

* * * * *